United States Patent [19]

Deller et al.

[11] 4,376,215
[45] Mar. 8, 1983

[54] PROCESS FOR THE PRODUCTION OF 4-AMINOBUTYRAMIDE HYDROCHLORIDE

[75] Inventors: Klaus Deller, Hainburg; Axel Kleemann, Hanau; Jürgen Martens, Alzenau; Horst Weigel, Rodenbach, all of Fed. Rep. of Germany

[73] Assignee: Degussa AG, Frankfurt am Main, Fed. Rep. of Germany

[21] Appl. No.: 321,702

[22] Filed: Nov. 16, 1981

[30] Foreign Application Priority Data

Dec. 18, 1980 [DE] Fed. Rep. of Germany ....... 3047753

[51] Int. Cl.³ .......................................... C07C 103/183
[52] U.S. Cl. .................................................... 564/198
[58] Field of Search ......................................... 564/198

[56] References Cited

U.S. PATENT DOCUMENTS 3,573,304  3/1971  Eberle et al. .................. 564/198 X
4,322,552  3/1982  Kleemann et al. .................. 564/198

OTHER PUBLICATIONS

Wagner et al., *Synthetic Organic Chemistry*, John Wiley & Sons, N.Y., N.Y., 1953, p. 570.
Farquharson et al., CA 55:23522c (1952).

*Primary Examiner*—Thomas A. Waltz
*Attorney, Agent, or Firm*—Cushman, Darby & Cushman

[57] ABSTRACT

4-aminobutyramide hydrochloride is produced by saponifying 4-(benzylamino)-or-4-(dibenzylamino)-butyronitrile to the corresponding substituted 4-aminobutyramide and subjecting this in the form of the hydrochloride in the presence of an inert solvent and a platinum metal catalyst to a hydrogenation treatment whereby the benzyl group or the two benzyl groups are split off.

17 Claims, No Drawings

PROCESS FOR THE PRODUCTION OF 4-AMINOBUTYRAMIDE HYDROCHLORIDE

SUMMARY OF THE INVENTION 4-aminobutyramide and derivatives thereof have great significance as therapeutics, especially as nerve transmitters.

The present invention is directed to a process for the production of 4-aminobutyramide hydrochloride comprising (a) saponifying a substituted butyronitrile of the formula

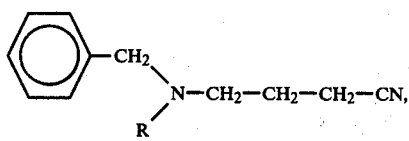

where R is hydrogen or a benzyl group to the corresponding butyramide of the formula

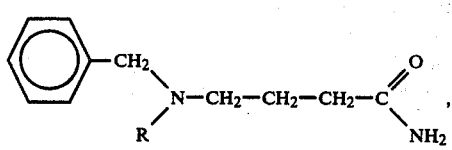

in which R is as defined above and (b) subjecting the butyramide of formula (II) in the form of the hydrochloride in the presence of an inert solvent and a platinum metal catalyst to a hydrogenation treatment.

The preferred starting material 4-(benzylamino)-butyronitrile and the 4-(dibenzylamino)-butyronitrile can be produced in known manner by the reaction of 4-chlorobutyronitrile with monobenzylamine or dibenzylamine (see J. Org. Chem. Vol. 32 page 738 (1967); J. Chem. Soc. (1955) pages 2371-2376). They can be employed in the form of the free base or as the acid addition salt, e.g., as the hydrochloride.

In reaction step (a) the butyronitrile of formula (I) is saponified in known manner to the corresponding butyramides of formula (II) which previously have not been described. The saponification, for example can take place by the action of 3 to 30 weight percent hydrogen peroxide in alkaline medium, e.g., sodium hydroxide or potassium hydroxide at a temperature of around 50° C. or through the action of manganese dioxide in an organic solvent, e.g., ethanol, methanol, isopropanol at room temperature.

However, quicker and more advantageous is an acid saponification in the presence of a mineral acid such as sulfuric acid or phosphoric acid and especially hydrochloric acid or hydrobromic acid, or of mixtures of a hydrohalic acid, especially hydrochloric acid or hydrobromic acid, and acetic acid. The saponification agent can be used for example in an amount between 200 and 1,000 ml, preferably between 250 and 500 ml, per mole of butyronitrile of formula (I). A suitable manner for example is to have the saponification agent present and then add the butyronitrile of formula (I) under stirring at a temperature, between −5° and +10° C., preferably between 0° and 5° C. For completion of the saponification reaction the reaction mixture is stirred, for example for 2 hours, whereby it is recommended to hold the temperature of the reaction mixture below 30° C.

Depending on the saponification conditions chosen the desired butyramide of formula (II) is obtained in the form of the free base or as the acid addition salt, e.g., as the hydrochloride or hydrobromide. It is employed in the form of the hydrochloride for the hydrogenation treatment in step (b). Thus in case it is not already present as the hydrochloride it is converted in known manner through addition of hydrochloric acid or through absorption on an acid ion exchanger and elution with hydrochloric acid into the hydrochloride.

The hydrogenation treatment is carried out in the presence of an inert solvent. Especially suited solvents are water, primary or secondary alcohols having up to 6, especially up to 4 carbon atoms or mixtures of water and such alcohols. Examples of such alcohols are alkanols such as methyl alcohol, ethyl alcohol, propyl alcohol, isopropyl alcohol, butyl alcohol, isobutyl alcohol, sec. butyl alcohol, amyl alcohol and hexyl alcohol. The solvent can be used for example in an amount between 5 and 100 ml, preferably between 10 and 100 ml per gram of butyramide of formula (II) employed.

The hydrogenation treatment furthermore requires the presence of a platinum metal catalyst. Especially preferred catalysts are platinum, rhodium, iridium or platinum (IV) oxide and particularly palladium. There can also be used mixtures of the platinum catalysts mentioned. The catalysts can be employed in free form or as carrier catalysts (e.g., precipitated on activated carbon). The amount of catalyst employed is not critical. For the realization of short reaction times, however, it is recommended to employ the platinum metal catalyst in an amount of 1 to 100, preferably from 2 to 10, weight percent, based on the butyramide of formula (II) employed.

The hydrogenation treatment suitably takes place at a temperature between 0° and 100° C., preferably between 40° and 60° C. It can be carried out without excess pressure by leading hydrogen through the reaction mixture, or in a pressure resistant vessel under a hydrogen pressure up to 100 bar. Preferably there are used hydrogen pressures up to 20 bar.

In the hydrogenation treatment the benzyl group or benzyl groups of the butyramide of formula (II) are split off in the form of toluene and there is formed directly in high yield the desired 4-aminobutyramide hydrochloride.

Unless otherwise indicated all parts and percentages are by weight.

The process can comprise, consist essentially of or consist of the stated steps with the recited materials.

The invention is explained in more detail through the following examples, namely reaction step (a) is illustrated in Examples 1 to 5 and reaction step (b) in Examples 6 to 19.

EXAMPLE 1

At 0° to 5° C. with stirring there were added 21 grams (0.1 mole) of 4-(benzylamino)-butyronitrile hydrochloride to 25 ml of concentrated hydrochloric acid. The reaction mixture was heated within one hour with stirring to 26° C. Reaction was allowed to continue at this temperature for another hour. The solution was added to 300 ml of isopropanol while stirred. Thereby a colorless crystallizate precipitated which was sucked off. The crystallizate was dried at 50° to 70° C. in a water jet vacuum. The yield was 16.9 grams (73.9% of theory) of 4-(benzylamino)-butyramide hydrochloride.

Melting Point: 189°–191° C.

Thin layer chromatogram (SiO$_2$:mobile phase n-butanol:glacial acetic acid:water=4:1:1): R$_F$ value=0.37.

IR-Spectrum (KBr-slug): ν(Amide) 1645 and 1595 cm$^{-1}$. In the region 2260 to 2210 cm$^{-1}$, typical for nitrile groups, no peak is present.

EXAMPLE 2

At 0° to 5° C. with stirring there were added 21 grams (0.1 mole) of 4-(benzylamino)-butyronitrile hydrochloride to 45 ml of concentrated hydrochloric acid. The reaction mixture was heated within two hours to 28° C. Subsequently the mixture was neutralized to pH 7 by addition of 50% aqueous sodium hydroxide solution. The solvent was vaporized under reduced pressure by heating to a maximum of 80° C. The resulting mixture of sodium chloride and 4-(benzylamino)-butyramide hydrochloride was extracted at 60° C. three times with 150 ml of absolute ethanol and the combined ethanol extracts were concentrated. There were obtained 18.5 grams (80.9%) of 4-(benzylamino)-butyramide hydrochloride as shining flakes.

Melting Point: 189°–191° C., after recrystallization from ethanol.

EXAMPLE 3

Example 1 was repeated with the difference that instead of hydrochloric acid there was employed a mixture of glacial acetic acid and hydrobromic acid as well as in place of 4-(benzylamino)-butyronitrile hydrochloride 0.1 mole of 4-(benzylamino)-butyronitrile as the free base. The yield of 4-(benzylamino)-butyramide hydrobromide was 20.3 grams, corresponding to 74.3% of theory Melting Point: 165°–166° C.

| Elemental analysis | Calculated (%) | | Found (%) |
|---|---|---|---|
| C$_{11}$H$_{17}$N$_2$OBr | C | 48,36 | 48,09 |
| (273,2) | H | 6,27 | 6,40 |
| | N | 10,26 | 10,21 |

EXAMPLE 4

Example 2 was repeated with the difference that in place of hydrochloric acid there were employed 30 ml of 35% hydrobromic acid as well as in place of the 4-(benzylamino)-butyronitrile hydrochloride 0.1 mole of 4-(benzylamino)-butyronitrile as the free base.

The yield of 4-(benzylamino)-butyramide hydrobromide was 16.5 grams, corresponding to 60.4% of theory. Melting Point: 165°–167° C.

EXAMPLE 5

Example 1 was repeated with the difference that in place of 4-(benzylamino)-butyronitrile hydrochloride there were employed 30 grams (0.1 mole) of 4-(dibenzylamino)-butyronitrile hydrochloride.

The yield of 4-(dibenzylamino)-butyramide hydrochloride was 15.0 grams, corresponding to 47.2% of theory IR-Spectrum (KBr-slug): ν (Amide) 1650 and 1595 cm$^{-1}$

| Elemental analysis | Calculated (%) | | Found (%) |
|---|---|---|---|
| C$_{18}$H$_{23}$ClN$_2$ (318,9) | C | 67,85 | 67,52 |
| | H | 7,27 | 7,51 |
| | N | 8,79 | 8,49 |

EXAMPLE 6

1 gram of 4-(benzylamino)-butyramide hydrochloride was dissolved in 90 ml of methanol, treated with 0.1 gram of palladium black and hydrogenated at 40° to 60° C. at normal pressure with hydrogen gas. After three hours the uptake of hydrogen was completed. The catalyst was filtered off and the filtrate concentrated to dryness on a rotary evaporator. The residue was recrystallized from ethanol. Yield: 0.60 gram (99% of theory).

Melting Point: 135°–138° C.

$^1$H-NMR (DMSO-d$_6$+CDCl$_3$): δ s, 8,25 (3H, NH$_3$), s 7,55 (1H, Amide), s 6,83 (1H, Amide), m 2,83 (2H, CH$_2$), m 2,22 (2H, CH$_2$) and m 1,90 (2H, CH$_2$) ppm.

EXAMPLE 7

Example 6 was repeated with the single difference that in place of methanol there was used ethanol as the solvent and the catalyst was sucked off at a temperature of 50° to 60° C. after the hydrogenation. Yield: 0.58 gram (95.7% of theory). Melting Point: 137°–138° C.

EXAMPLE 8

Example 7 was repeated with the difference that there were used only 10 ml of ethanol as the solvent and the filtration was at 10° C. The filter cake (mixture of 4-aminobutyramide hydrochloride and catalyst) was treated with 50 ml of warm methanol and combined with the filtrate. This combination was concentrated to dryness and after recrystallization from ethanol there were obtained 0.59 grams (97.4% of theory) of 4-aminobutyramide hydrochloride. Melting Point: 134°–137° C.

EXAMPLE 9

Example 6 was repeated with the single difference that in place of methanol there were employed 50 ml of water as solvent. Yield: 0.50 gram (82.5% of theory). Melting point: 133°–136° C.

EXAMPLE 10

Example 6 was repeated with the single difference that in place of methanol there were employed 50 ml of a mixture of equal parts by volume of water and ethanol as solvent. Yield: 0.52 gram (85.8% of theory). Melting Point: 134°–136° C.

EXAMPLE 11

Example 8 was repeated with the single difference that in place of ethanol there were employed 80 ml of isopropyl alcohol as the solvent Yield: 0.49 gram (80.9% of theory). Melting Point: 134°–137° C.

EXAMPLE 12

Example 8 was repeated with the single difference that in place of ethanol there were employed 70 ml of n-butanol as the solvent. Yield: 0.49 gram (80.9% of theory). Melting Point: 135°–137° C.

EXAMPLE 13

Example 6 was repeated with the single difference that in place of palladium black there was employed 0.1 gram of metallic platinum. Yield: 0.53 gram (87.5% of theory). Melting Point: 136°–138° C.

EXAMPLE 14

Example 8 was repeated with the sole difference that in place of palladium black there was employed 0.05 gram of metallic rhodium. Yield: 0.53 gram (87.5% of theory). Melting Point: 136°–138° C.

EXAMPLE 15

Example 6 was repeated with the sole difference that in place of palladium there was employed 0.2 gram of a preparation of palladium and activated carbon having a noble metal content of 5 weight percent. Yield: 0.49 gram (80.9% of theory). Melting Point: 134°–137° C.

EXAMPLE 16

Example 10 was repeated with the sole difference that in place of palladium there was employed 0.1 gram of metallic iridium. Yield: 0.52 gram (85.8% of theory). Melting Point: 135°–138° C.

EXAMPLE 17

Example 10 was repeated with the sole difference that the hydrogenation was carried out in a shaking autoclave at a hydrogen pressure of 5 bar. Yield: 0.59 grams (97.4% of theory). Melting Point: 135°–137° C.

EXAMPLE 18

Example 6 was repeated with the sole difference that the hydrogenation was carried out in a shaking autoclave at a hydrogen pressure of 18 bar. Yield: 0.60 gram (99.0% of theory).
Melting Point: 136°–139° C.

EXAMPLE 19

Example 6 was repeated with the sole difference that the substrate 4-(benzylamino)-butyramide hydrochloride was replaced by 1 gram of 4-(dibenzylamino)-butyramide hydrochloride. Yield of 4-aminobutyramide hydrochloride 0.41 gram (96.8% of theory). Melting Point: 137°–138° C.

The entire disclosure of German priority application No. P 3047753.3-42 is hereby incorporated by reference.

What is claimed is:

1. A process for the production of 4-aminobutyramide comprising (a) saponifying a substituted butyronitrile of the formula

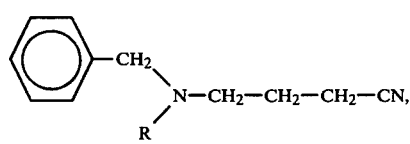

(I)

in which R is hydrogen or a benzyl group, or an acid addition salt thereof to the corresponding butyramide of the formula $$\text{C}_6\text{H}_5\text{-CH}_2\text{-N(R)-CH}_2\text{-CH}_2\text{-CH}_2\text{-C(=O)-NH}_2$$ (II)

or an acid addition salt thereof, (b) if the butyramide of formula (II) is not in the form of the hydrochloride converting it to the hydrochloride, and (c) subjecting the hydrochloride of the butyramide of formula (II) in the presence of an inert solvent and a platinum group metal catalyst to hydrogenation.

2. A process according to claim 1 wherein the saponification in reaction step (a) is carried out by means of a mineral acid or a mixture of a hydrohalic acid and glacial acetic acid at a temperature between −5° and +30° C.

3. A process according to claim 1 wherein the saponification is carried out by means of hydrochloric acid, hydrobromic acid or a mixture of acetic acid with either hydrochloric acid or hydrobromic acid.

4. A process according to claim 3 wherein the saponification is carried out by means of hydrochloric acid or a mixture of hydrochloric acid and acetic acid.

5. A process according to claim 2 wherein in reaction step (c) the hydrogenation treatment is carried out in the presence of water, a primary or secondary alcohol having up to 6 carbon atoms or a mixture of water and such an alcohol as solvent.

6. A process according to claim 1 wherein in reaction step (c) the hydrogenation treatment is carried out in the presence of water, a primary or secondary alcohol having up to 6 carbon atoms or a mixture of water and such an alcohol as solvent.

7. A process according to claim 6 wherein the alcohol is an alkanol of 1 to 4 carbon atoms.

8. A process according to claim 5 wherein the alcohol is an alkanol of 1 to 4 carbon atoms.

9. A process according to claim 6 wherein the hydrogenation in step (c) is carried out in the presence of palladium.

10. A process according to claim 5 wherein the hydrogenation in step (c) is carried out in the presence of palladium.

11. A process according to claim 2 wherein the hydrogenation in step (c) is carried out in the presence of palladium.

12. A process according to claim 1 wherein the hydrogenation in step (c) is carried out in the presence of palladium.

13. A process for the production of 4-aminobutyramide hydrochloride comprising hydrogenating the hydrochloride of a butyramide of the formula $$\text{C}_6\text{H}_5\text{-CH}_2\text{-N(R)-CH}_2\text{-CH}_2\text{-CH}_2\text{-C(=O)-NH}_2$$ (II)

where R is hydrogen or a benzyl group in the presence of an inert solvent and a platinum group metal catalyst.

14. A process according to claim 13 wherein the solvent is water, a primary or secondary alkanol having 1 to 6 carbon atoms or a mixture of water and such an alkanol.

15. A process according to claim 14 wherein the alkanol has 1 to 4 carbon atoms.

16. A process according to claim 15 wherein the catalyst is palladium, platinum, rhodium, iridium or platinum (IV) oxide.

17. A process according to claim 16 wherein the catalyst is palladium.

* * * * *